United States Patent [19]
Lebrun et al.

[11] Patent Number: 5,510,471
[45] Date of Patent: Apr. 23, 1996

[54] CHIMERIC GENE FOR THE TRANSFORMATION OF PLANTS

[75] Inventors: Michel Lebrun, Lyons; Bernard Leroux, Lozanne; Alain Sailland, Lyons, all of France

[73] Assignee: Rhone-Poulenc Agrochimie, Lyons, France

[21] Appl. No.: 251,621

[22] Filed: May 31, 1994

Related U.S. Application Data

[63] Continuation of Ser. No. 846,211, Mar. 4, 1992, abandoned.

[30] Foreign Application Priority Data

Mar. 5, 1991 [FR] France ..................... 91 02872

[51] Int. Cl.$^6$ ................. C07H 17/00; C12N 15/00; C12N 15/29; C12N 15/82
[52] U.S. Cl. .................. 536/23.4; 536/23.6; 435/69.1; 435/172.3; 435/69.7
[58] Field of Search ................. 800/205; 536/23.4, 536/23.6; 435/172.3, 69.7, 69.1; 935/11

[56] References Cited

FOREIGN PATENT DOCUMENTS 8802402  4/1988  WIPO.

OTHER PUBLICATIONS

Smeekens et al. (1990) TIBS 15: 73–76.
LeBrun et al. (1987) Nucl. Acids Res. 15(10): 4360.
Waksman et al. (1987) Nucl. Acids Res. 15(17): 7181.
L. Comai, et al. (1988) *The Journal of Biological Chemistry* vol. 263, No. 29 Issue of Oct. 15, pp. 15104–15109, "Chloroplast Transport of a Ribulose Bisphosphate Carboxylase Small Subunit–5–Enolpyruvyl 3–Phosphoshikimate Synthase Chimeric Protein Requires Part of the Mature Small Subunit in Addition to the Transit Preptide".

*Primary Examiner*—David T. Fox
*Assistant Examiner*—Elizabeth F. McElwain
*Attorney, Agent, or Firm*—Scully, Scott, Murphy & Presser

[57] ABSTRACT

Chimeric gene for conferring to plants an increased tolerance to a herbicide having as its target EPSPS comprises, in the direction of transcription, a promoter region, a transit peptide region, a coding sequence for glyphosate tolerance and a polyadenylation signal region, wherein the transit peptide region comprises, in the direction of translation, at least one transit peptide of a plant gene encoding a plastid-localised enzyme, a partial sequence of the N-terminal mature part of a plant gene encoding a plastid-localised enzyme and then a second transit peptide of a plant gene encoding a plastid- localised enzyme. Production of glyphosate-tolerant plants is disclosed.

11 Claims, No Drawings

CHIMERIC GENE FOR THE TRANSFORMATION OF PLANTS

This is a continuation of application Ser. No. 846,211 filed on Mar. 4, 1992, now abandoned.

BACKGROUND OF THE INVENTION

The present invention relates to novel transit peptide DNA sequences, to novel chimeric genes and to their use in plants for conferring to them an increased tolerance to herbicides in general especially to those of the phosphonomethylglycine family. It also relates to the plant cells transformed by these genes, to the transformed plants regenerated from these cells as well as to the plants derived from crossbreedings using these transformed plants.

Glyphosate, sulfosate or fosametine are broad-spectrum systemic herbicides of the phosphonomethyl-glycine family. They act essentially as competitive inhibitors of 5-(enolpyruvyl)shikimate-3-phosphate synthase (EC 2.5.1.19) or EPSPS in relation to PEP (phosphoenolpyruvate). After their application to the plant, they are translocated inside the plant where they accumulate in the rapidly growing parts, in particular the caulinary and root apexes, causing the deterioration and even the destruction of sensitive plants.

Plastidial EPSPS, the main target of these products, is an enzyme of the aromatic amino acid biosynthesis pathway which is encoded by one or more nuclear genes and synthesised in the form of a cytoplasmic precursor and then imported into the plastids where it accumulates in its natural form.

The tolerance of plants to glyphosate and to products of the family is obtained by the stable introduction inside their genome of an EPSPS gene of plant or bacterial origin mutant or nonmutant with respect to the characteristics of the inhibition of the product of this gene by glyphosate. Given the mode of action of glyphosate and the degree of tolerance to glyphosate of the product of the genes used, it is useful to be able to express the product of translation of this gene so as to permit its substantial accumulation in plastids.

It is known, for example from U.S. Pat. No. 4,535,060, to confer to a plant a tolerance to a herbicide of the above-mentioned type, in particular N-(phosphonomethyl)glycine or glyphosate, by introducing into the plant genome a gene encoding an EPSPS carrying at least one mutation making this enzyme more resistant to its competitive inhibitor (glyphosate), after localisation of the enzyme in the plastidial compartment. However, these techniques need to be improved in order to achieve greater reliability in the use of these plants under agronomic conditions.

SUMMARY OF THE INVENTION

In the present description, "plant" is understood as meaning any differentiated multicellular organism capable of photosynthesis and "plant cell" any cell derived from a plant and capable of forming undifferentiated tissues such as calluses or differentiated tissues such as embryos or plant sections, plants or seeds.

The subject of the present invention is the production of transformed plants having an increased tolerance to herbicides in general and especially to those of the phosphonomethylglycine family by regenerating cells transformed by means of novel chimeric genes comprising a gene for tolerance to these herbicides. The invention also relates to these novel chimeric genes, to the novel transit peptides which they contain as well as to the plants containing them which are made more tolerant by an accumulation of the mutant enzyme, in its mature form, in the plants.

More particularly, the subject of the invention is a chimeric gene for conferring to plants an increased tolerance to a herbicide whose target is EPSPS, comprising, in the direction of transcription, a promoter region, a transit peptide region, a sequence of a gene encoding a glyphosate tolerance enzyme and an untranslated polyadenylation signal region at the 3' terminus, wherein the transit peptide region comprises, in the direction of transcription, a transit peptide of a plant gene encoding a plastid-localised enzyme, a partial sequence of the N-terminal mature part of a plant gene encoding a plastid-localised enzyme and then a second transit peptide of a plant gene encoding a plastid-localised enzyme.

The invention also relates to any DNA sequence of the transit peptide region defined above.

The transit peptides which can be used in the transit peptide region may be known per se and may be of plant origin, for example, derived from maize, sunflower, peas, tobacco or the like. The first and the second transit peptides may be identical, analogous or different. They may in addition each comprise one or more transit peptide units. A sequence derived from the SSU of the ribulose 1,5-diphosphate carboxylase oxygenase CRuBisCO) gene is preferably used.

The partial sequence of the N-terminal mature part is derived from a plant gene encoding a plastid-localised enzyme, such as for example a maize, sunflower or pea gene or the like, it being possible for the original plant species to be identical, analogous or different from that from which the first and second transit peptides are derived respectively. Furthermore, the partial sequence of the mature pan may comprise a varying number of amino acids, generally from 10 to 40, preferably from 18 to 33. A sequence derived from the SSU of the ribulose 1,5-diphosphate carboxylase oxygenase (RuBisCO) gene is preferably used.

Construction of the entire transit region may be carried out in a manner known per se, in particular by fusion or any other suitable means. The role of this characteristic region is to enable the release of a mature, native protein with a maximum efficiency.

The coding sequence for herbicide tolerance which may be used in the chimeric gene according to the invention encodes a mutant EPSPS having a degree of glyphosate tolerance. This sequence, obtained in particular by mutation of the EPSPS gene, may be of bacterial origin, for example derived from *Salmonella typhymurium* (and called in the text which follows "AroA gene"), or of plant origin, for example from petunia or from tomatoes. This sequence may comprise one or more mutations, for example the Pro 101 to Ser mutation or alternatively the Gly 96 to Ala mutations.

The promoter region of the chimeric gene according to the invention may consist advantageously of at least one promoter on a fragment thereof of a gene which is expressed naturally in plants, that is to say promoters of viral origin such as that of 35S RNA of the cauliflower mosaic virus (CaMV35S) or of plant origin such as the small subunit of the ribulose 1,5-diphosphate carboxylase (RuBisCO) gene of a crop such as maize or sunflower.

The untranslated polyadenylation signal region at the 3' terminus of the chimeric gene according to the invention may be of any origin, for example bacterial, such as the nopaline synthase gene, or of plant origin, such as the small subunit of the maize or sunflower RuBisCO.

The chimeric gene according to the invention may comprise, in addition to the above essential parts, an untranslated intermediate region (linker) between the promoter region and the coding sequence which may be of any origin, bacterial, viral or plant.

DESCRIPTION OF THE PREFERRED EMBODIMENTS

EXAMPLE 1

Construction of a Chemeric Gene

The construction of the chimeric gene according to the invention is carried out using the following elements:

1) "Double CaMV" promoter (that is to say part of which has been duplicated): The CaMV35S promoter was isolated by Odell et al (1985). A clone, pJO 5-2, containing about 850 bp upstream of the site of initiation of transcription was cut with EcoRI-HindIII, the ends of this isolated fragment were made blunt using Klenow polymerase and the fragment inserted at the HincII site of the vector pUC19 (Yannish-Perron et al., 1985). This promoter was digested with ClaI, the ends filled using Klenow polymerase and then redigested with HindIII. A HindIII-EcoRV fragment, isolated from the same initial promoter, was introduced between these two sites. The promoter thus obtained possesses a double amplification region upstream of the regulatory elements of the CaMV35S promoter. It was introduced in the form of a HindIII-EcoRI fragment into the vector pRPA-BL 150 A alpha 2, described in French Patent Application 88/04130, cut with HindIII and EcoRI.

2) Transfer region: the two transit peptides as well as the mature protein elements used are derived from the cloned cDNA of the small subunit of the gene of maize RuBisCO whose gene has been described by Lebrun et at. (1987), and from the cloned cDNA of the small subunit of the gene of sunflower RuBisCO, isolated by Waksman et al. (1987). More specifically, the transit region, called optimised transit peptide, comprises, in the direction of translation:

a transit peptide of the small subunit of sunflower RuBisCO, an N-terminal sequence of 22 amino acids of the mature part of the small subunit of maize RuBisCO, a transit peptide of the small subunit of maize RuBisCO.

The construct using this optimised transfer peptide is called pRPA-BL 410.

Other similar sequences may be used which contain sequences of 10 to 40 and preferably 18 and 33 amino acids respectively.

In order to provide a comparative element, another construction was carded out using a first transit peptide and the same mature sequence part but without a second transit peptide, according to the prior art (pRPA-BL 294).

3) Structural gene: it is derived from the mutant gene at the position (Pro 101 to Ser) of EPSPS of *Salmonella typhymurium* isolated by Stalker et al. (1985). The pMG34-2 clone (provided by Calgene) was linearised with XbaI and then treated with *Vigna radiata* nuclease. After recutting with SmaI, the two blunt ends were ligated. The clone obtained possesses an NcoI site in the initiator ATG as well as a 17-bp SalI site downstream of the stop codon. This clone was called pRPA-BL 104.

4) Polyadenylation signal region: the fragment is derived from the nopaline synthase gene of pTi37 (Bevan et al., 1983). This site is contained in a 260-bp MboI fragment (Fraley et al., 1983; Patent Application PCT 84/02913) which was treated with Klenow polymerase and cloned in the SmaI site of M13 mp 18 in order to introduce the BamHI and EcoRI sites at the 5' and 3' ends respectively.

After cutting with BamHI and treating with *Vigna radiata* nuclease followed by cutting with EcoRI and treating with Klenow polymerase, the resulting fragment was introduced in the vector p-BL 20 (cf. French Patent Application 88/04130), cut by XbaI and BamHI and treated with Klenow polymerase. After recutting with SalI and SstI, a fragment of about 0.4 kbp containing the 3' nos sequence on the side of the SalI site and the right end on the T-DNA side of the SstI site is obtained.

The assembly of the various elements was carried out in the following manner:

"Transit peptide of the SSU of the maize RuBisCO/AroA gene" fusion:

The transit peptide of the SSU of the maize RuBisCO gene is derived from a 192-bp EcoRI-SphI fragment obtained from the cDNA corresponding to the SSU gene of the maize RuBisCO gene, described by Lebrun et al. (1987), possessing an NcoI site spanning the initiation codon for translation and an SphI site corresponding to the cleavage site of the transit peptide.

Translational fusion is obtained between the maize transit peptide and the bacterial EPSPS gene by treating the SphI end with bacteriophage T4 polymerase and by ligating it with the Klenow polymerase-treated NcoI end of the AroA gene from pRPA-BL 104, recut with EcoRI.

Transit peptide of the SSU of maize RuBisCO/sequence of 22 amino acids of the mature part of the SSU of maize RuBisCO/AroA gene fusion:

Similarly, a 228-bp EcoRI-HindII fragment of the cDNA of the SSU of the maize RuBisCO gene is ligated with the Klenow polymerase-treated NcoI end of the AroA gene from pRPA-BL 104 and recut with EcoRI. A translational fusion is obtained between the transit peptide of the SSU of maize RuBisCO, the 22 amino acids of the mature part of the SSU of maize RuBisCO and the bacterial EPSPS gene.

Transit peptide of the SSU of sunflower RuBisCO:

The fragment is derived from the cDNA isolated by Waksman and Freyssinet (1987). An SphI site was created at the cleavage site of the transit peptide according to the method of Zoller and Smith (1984). The transit peptide of the SSU of sunflower RuBisCO thus obtained is a 171-bp EcoRI-SphI fragment.

Transit peptide of the SSU of sunflower RuBisCO/sequence of 22 amino acids of the mature part of the SSU of maize RuBisCO/AroA gene fusion:

The construct containing the transit peptide of the SSU of maize RuBisCO/sequence of 22 amino acids of the SSU of maize RuBisCO of the mature pan of the maize gene fusion was cut with 171-bp EcoRI-SphI corresponding to the transit peptide of the SSU of sunflower RuBisCO. A resulting construct exhibits a substitution of the EcoRI-SphI fragments and is a translational fusion "transit peptide of the SSU of sunflower RuBisCO/sequence of 22 amine acids of the mature part of the SSU of maize RuBisCO/AroA gene".

The EcoRI-SalI fragment was ligated with the SalI-SstI fragment containing the 3' nos sequence and the right end of the T-DNA. The resulting EcoRI-SstI fragment, comprising "transit peptide of the SSU of sunflower RuBisCO/sequence of 22 amine acids of the mature part of the SSU of maize RuBisCO/AroA gene/3' nos/T-DNA right end", is substituted for the EcoRI-SstI fragment containing the right end of the T-DNA of the plasmid 150 A alpha 2 containing the double CaMV promoter. The transcriptional fusion "double CaMV/transit peptide of the SSU of sunflower RuBisCO/sequence of 22 amine acids of the mature part of the SSU of maize RuBisCO/AroA gene/3' nos" in the vector 150 A alpha 2 was called pRPA-BL 294. "Transit peptide of the SSU of Sunflower RuBisCO/sequence of 22 amine acids of the SSU of maize RuBisCO/transit peptide of the SSU of maize RuBisCO/AroA gene" fusion:

The above construct is cut with NcoI-HindIII, releasing the Area gene. Next it is ligated with a 1.5 kbp NcoI-HindIII fragment containing the "transit peptide of the SSU of maize RuBisCO/AroA gene" fusion. A resulting construct exhibits a substitution of the NcoI-HindIII fragments and is a translational fusion "transit peptide of the SSU of sunflower RuBisCO/sequence of 22 amine acids of the SSU of the RuBisCO of the mature part of the maize gene/transit peptide of the SSU of maize RuBisCO/AroA gene".

The EcoRI-SalI fragment was ligated with the SalI-SstI fragment containing the 3' nos sequence and the right end of the T-DNA. The resulting EcoRI-SstI fragment comprising "transit peptide of the SSU of sunflower RuBisCO/sequence of 22 amino acids of the SSU of the RuBisCO of the mature part of the maize gene/transit peptide of the SSU of maize RuBisCO/AroA gene/3' nos/TDNA fight end" is substituted for the EcoRI-SstI fragment containing the right end of the T-DNA of the plasmid 150 A alpha 2 containing the double CaMV promoter. The transcriptional fusion "double CaMV/transit peptide of the SSU of sunflower RuBisCO/sequence of 22 amino acids of the SSU of the RuBisCO of the mature part of the maize gene/transit peptide of the SSU of maize RuBisCO/AroA gene/3' nos" in the vector 150 A alpha 2 was called pRPA-BL 410.

EXAMPLE 2

Resistance of the Transformed Plants

1. Transformation:

The vector is introduced into the nononcogenic agrobacterium strain EHA 101 (Hood et al., 1987) carrying the cosmid pTVK 291 (Komari et al., 1986). The transformation method is based on the procedure of Horsh et al. (1985).

2. Regeneration:

The regeneration of the tobacco PBD6 (source SEITA France) using foliar explants is carried out on a Murashige and Skoog (MS) basic medium containing 30 g/l of sucrose and 200 g/ml of kanamycin. The foliar explants are removed from greenhouse- or in vitro-grown plants and transformed according to the foliar disc method (Science 1985, Vol. 227, p. 1229–1231) in three successive stages: the first comprises the induction of shoots on an MS medium supplemented with 30 g/l of sucrose containing 0.05 mg/l of naphthylacetic acid (ANA) and 2 mg/l of benzylaminopurine (BAP), for 15 days. The shoots formed during this stage are then developed by culturing on an MS medium supplemented with 30 g/l of sucrose, but not containing; hormone, for 10 days. The developed shoots are then removed and they are cultured on an MS planting medium containing half the content of salts, vitamins and sugars and not containing hormone. After about 15 days, the deeply-rooted shoots are placed in soil.

3. Measurement of the glyphosate tolerance:

a) In vitro: the tolerance is measured by weighing the mass of calluses extrapolated to 100 foliar discs of 0.5 cm in diameter, after 30 days of growth on an MS medium supplemented with 30 g/l of sucrose, 0.05 mg/l of naphthaleneacetic acid and 2 mg/l of BAP containing 35 ppm of glyphosate and 200 micrograms/ml of kanamycin. Under these conditions, it is observed that for the tobacco plants modified by the chimeric gene of pRPA BL 410 according to the invention, the mass of calluses is 34 g whereas for the plants modified by the chimeric gene without a second transit peptide, the mass is only 12 g.

b) In vivo: 30 plants derived from the regeneration of the tobaccos transformed using pRPA-BL 294 and pRPA-BL 410 respectively are transferred to a greenhouse and treated at the 5-leaf stage by spraying with an aqueous suspension at a dose corresponding to 0.6 kg/ha of glyphosate (Round up). After 21 days, a phenotypic examination is carried out of the plants relative to untransformed control plants. Under these conditions, it is observed that the plants transformed using pRPA-BL 410 possess a negligible phytotoxicity whereas the control plants are completely destroyed; moreover, the plants transformed using a chimeric gene, which differs from the preceding one by the absence of a second transit peptide, possess a phytotoxicity of not less than 30% destruction.

These results clearly show the improvement brought by the use of a chimeric gene according to the invention for the same gene encoding the glyphosate tolerance.

The transformed plants according to the invention may be used as parents for producing lines and hybrids having an increased tolerance to glyphosate.

EXAMPLE 3

Spring colzas, Westar cultivar, resistant to glyphosate, were obtained using the method of BOULTER et al., 1990 (Plant Science, 70: 91–99), with pRPA-BL 410. These plants were resistant to a greenhouse treatment with glyphosate at 400.

g a.s/ha, a treatment which destroys nontransgenic plants.

We claim:

1. A nucleic acid construct which codes for a polypeptide sufficient for localization of a gene product in a chloroplast of a plant cell which polypeptide comprises a fusion which in the direction of translation comprises a first chloroplast transit peptide from a ribulose-1,5-bisphosphate carboxylase small subunit, an N-terminal domain of a mature ribulose-1,5-bisphosphate carboxylase small subunit protein and a second chloroplast transit peptide from a ribulose-1,5-bisphosphate carboxylase small subunit.

2. The nucleic acid construct of claim 1 wherein said first chloroplast transit peptide and said second chloroplast transit peptide have identical amino acid sequences.

3. The nucleic acid construct of claim 1 wherein said first chloroplast transit peptide and said second chloroplast transit peptides each have different amino acid sequences.

4. The nucleic acid construct of claim 1 wherein said first or second transit peptide is a transit peptide of a maize ribulose-1,5-bisphosphate carboxylase small subunit.

5. The nucleic acid construct of claim 1 wherein said N-terminal domain is an N-terminal domain of a mature maize ribulose-1,5-bisphosphate carboxylase small subunit.

6. The nucleic acid construct of claim 1 wherein said first or second transit peptide and said N-terminal domain are from the same 1,5-bisphosphate carboxylase small subunit protein.

7. The nucleic acid construct of claim 1 wherein said first or second transit peptide is a transit peptide of a sunflower ribulose-1,5-bisphosphate carboxylase small subunit.

8. The nucleic acid construct of claim 1 wherein said N-terminal domain is an N-terminal domain of mature sunflower ribulose-1,5-bisphosphate carboxylase small subunit.

9. The nucleic acid construct of any of claims 1, 5, 6 or 8 wherein said N-terminal domain comprises about 10 to about 40 amino acids.

10. The nucleic acid construct of any of claim 1, 5, 6 or 8 wherein said N-terminal domain comprises about 18 to about 33 amino acids.

11. A nucleic acid construct which codes for a polypeptide sufficient for localization of a gene product in a chloroplast of a plant cell which polypeptide comprises a fusion which in the direction of translation comprises a first chloroplast transit peptide from a sunflower ribulose-1,5-bisphosphate carboxylase small subunit, approximately 22 amino acids from the N-terminal region Of a mature maize ribulose-1, 5-bisphosphate carboxylase small subunit and a second chloroplast transit peptide from a maize ribulose-1,5-bisphosphate carboxylase small subunit.

* * * * *

UNITED STATES PATENT AND TRADEMARK OFFICE
CERTIFICATE OF CORRECTION

PATENT NO. : 5,510,471
DATED : April 23, 1996
INVENTOR(S) : Michel Lebrun, et al.

It is certified that error appears in the above-indentified patent and that said Letters Patent is hereby corrected as shown below:

Column 2, line 27: "CRuBisCo)" should read --(RuBisCo)--

Column 2, line 35: "pan" should read --part--

Column 3, line 13: "Chemeric" should read --Chimeric--

Column 3, line 22: "HincII" should read --HincII--

Column 3, line 53: "carded" should read --carried--

Column 4, line 52: "pan" should read --part--

Column 4, lines 57 & 63: "amine" should read --amino--

Column 5, lines 2, 5 & 14: "amine" should read --amino--

Column 5, line 5: "Sunflower" should read --sunflower--

Column 5, line 9: "Area" should read --AroA--

Column 5, line 23: "TDNA fight" should read --T-DNA right--

UNITED STATES PATENT AND TRADEMARK OFFICE
CERTIFICATE OF CORRECTION

PATENT NO. : 5,510,471
DATED : April 23, 1996
INVENTOR(S) : Michel Lebrun, et al.

It is certified that error appears in the above-indentified patent and that said Letters Patent is hereby corrected as shown below:

Column 5, line 55: after "containing" delete --;--
Column 6, line 33: after "400" delete --.--

Column 7, line 4, Claim 10: "claim" should read --claims--
Column 8, line 4, Claim 11: "Of" should read --of--

Signed and Sealed this

Twenty-fourth Day of December, 1996

Attest:

BRUCE LEHMAN

Attesting Officer

Commissioner of Patents and Trademarks